(12) United States Patent
Chann et al.

(10) Patent No.: US 10,256,595 B2
(45) Date of Patent: Apr. 9, 2019

(54) WIDELY TUNABLE INFRARED SOURCE SYSTEM AND METHOD

(71) Applicants: Bien Chann, Merrimack, NH (US); Robin Huang, Wakefield, MA (US); Parviz Tayebati, Sherborn, MA (US)

(72) Inventors: Bien Chann, Merrimack, NH (US); Robin Huang, Wakefield, MA (US); Parviz Tayebati, Sherborn, MA (US)

(73) Assignee: TERADIODE, INC., Wilmington, MA (US)

( * ) Notice: Subject to any disclaimer, the term of this patent is extended or adjusted under 35 U.S.C. 154(b) by 0 days.

(21) Appl. No.: 15/800,429

(22) Filed: Nov. 1, 2017

(65) Prior Publication Data

US 2018/0097334 A1   Apr. 5, 2018

Related U.S. Application Data

(63) Continuation of application No. 13/923,344, filed on Jun. 20, 2013, now Pat. No. 9,865,985.
(Continued)

(51) Int. Cl.
*H01S 3/10* (2006.01)
*H01S 3/105* (2006.01)
(Continued)

(52) U.S. Cl.
CPC ........... *H01S 3/105* (2013.01); *B01L 3/50851* (2013.01); *B01L 2200/147* (2013.01); *B01L 2300/046* (2013.01); *B01L 2300/0654* (2013.01); *B01L 2300/0851* (2013.01); *G01N 1/31* (2013.01); *G01N 1/38* (2013.01); *H01S 3/0085* (2013.01); *H01S 3/0635* (2013.01); *H01S 3/08009* (2013.01); *H01S 3/0812* (2013.01); *H01S 3/10* (2013.01); *H01S 3/101* (2013.01);
(Continued)

(58) Field of Classification Search
CPC ...... H01S 3/105; H01S 2301/20; H01S 3/101; H01S 3/10; H01S 5/0071; H01S 5/0085; H01S 5/02292; H01S 3/0085; H01S 5/06253; H01S 5/4012; H01S 5/02288; H01S 5/143; H01S 3/0635; H01S 3/081; B01L 2200/147
USPC .......................................................... 372/20
See application file for complete search history.

(56) References Cited

U.S. PATENT DOCUMENTS 6,044,096 A    3/2000   Wolak et al.
6,192,062 B1   2/2001   Sanchez-Rubio et al.
(Continued)

FOREIGN PATENT DOCUMENTS

JP   2007165624 A    6/2007
WO   2006/045303 A2  5/2006
(Continued)

*Primary Examiner* — Vu A Vu
(74) *Attorney, Agent, or Firm* — Morgan, Lewis & Bockius LLP

(57) ABSTRACT

A system and method for tuning and infrared source laser in the Mid-IR wavelength range. The system and method comprising, at least, a plurality of individually tunable emitters, each emitter emitting a beam having a unique wavelength, a grating, a mirror positioned after the grating to receive at least one refracted order of light of at least one beam and to redirect the beam back towards the grating, and a micro-electro-mechanical systems device containing a plurality of adjustable micro-mirrors.

20 Claims, 6 Drawing Sheets

Related U.S. Application Data

(60) Provisional application No. 61/661,836, filed on Jun. 20, 2012.

(51) Int. Cl.

| | |
|---|---|
| G01N 1/38 | (2006.01) |
| B01L 3/00 | (2006.01) |
| G01N 1/31 | (2006.01) |
| H01S 3/08 | (2006.01) |
| H01S 3/081 | (2006.01) |
| H01S 3/063 | (2006.01) |
| H01S 3/1055 | (2006.01) |
| H01S 5/14 | (2006.01) |
| H01S 5/022 | (2006.01) |
| H01S 5/40 | (2006.01) |
| H01S 5/0625 | (2006.01) |
| H01S 3/00 | (2006.01) |
| H01S 5/00 | (2006.01) |
| H01S 3/101 | (2006.01) |

(52) U.S. Cl.
CPC ......... *H01S 3/10023* (2013.01); *H01S 3/1055* (2013.01); *H01S 5/0071* (2013.01); *H01S 5/0085* (2013.01); *H01S 5/02288* (2013.01); *H01S 5/02292* (2013.01); *H01S 5/06253* (2013.01); *H01S 5/143* (2013.01); *H01S 5/4012* (2013.01); *H01S 2301/20* (2013.01)

(56) References Cited

U.S. PATENT DOCUMENTS

| | | | |
|---|---|---|---|
| 6,356,576 B1 | 3/2002 | Smith | |
| 6,687,275 B2 * | 2/2004 | Lin | H01S 5/1032 372/101 |
| 6,810,165 B2 * | 10/2004 | Golub | G02B 6/266 359/333 |
| 7,177,496 B1 * | 2/2007 | Polynkin | G01J 3/32 385/18 |
| 7,394,842 B2 * | 7/2008 | Glebov | H01S 5/40 372/102 |
| 7,463,664 B2 * | 12/2008 | Mizuuchi | G02B 6/1228 372/22 |
| 7,949,030 B2 * | 5/2011 | Volodin | H01S 5/065 359/27 |
| 8,049,966 B2 | 11/2011 | Chann | |
| 2004/0095983 A1 | 5/2004 | Whitley | |
| 2004/0174604 A1 | 9/2004 | Brown | |
| 2004/0252744 A1 | 12/2004 | Anikitchev et al. | |
| 2006/0092994 A1 * | 5/2006 | Frankel | H01S 3/105 372/18 |
| 2006/0126690 A1 | 6/2006 | Kido et al. | |
| 2007/0002925 A1 | 1/2007 | Zediker | |
| 2010/0110556 A1 * | 5/2010 | Chann | H01S 5/4062 359/619 |
| 2011/0058176 A1 | 3/2011 | Pflugl et al. | |
| 2011/0216417 A1 | 3/2011 | Chann et al. | |
| 2011/0216792 A1 | 3/2011 | Chann et al. | |
| 2011/0310921 A1 | 8/2011 | Chann et al. | |
| 2011/0305250 A1 | 12/2011 | Chann et al. | |
| 2011/0305256 A1 | 12/2011 | Chann et al. | |
| 2012/0105968 A1 | 5/2012 | Chann et al. | |
| 2013/0208361 A1 | 8/2013 | Chann et al. | |

FOREIGN PATENT DOCUMENTS

| | | |
|---|---|---|
| WO | 2006097531 A1 | 9/2006 |
| WO | 2011109760 A3 | 11/2011 |

* cited by examiner

WIDELY TUNABLE INFRARED SOURCE SYSTEM AND METHOD

CROSS-REFERENCE TO RELATED APPLICATIONS

This application is a continuation of U.S. patent application Ser. No. 13/923,344, filed Jun. 20, 2013, which claims the benefit of and priority to U.S. Provisional Patent Application No. 61/661,836, filed Jun. 20, 2012, the entire disclosure of each of which is hereby incorporated herein by reference.

BACKGROUND OF THE INVENTION

1. Field of the Invention

The present embodiments relate generally to laser systems and more particularly to widely tunable infrared source (WTIRS) laser systems and methods.

2. Description of the Prior Art

Widely tunable infrared source lasers are a special class of Wavelength beam combining (WBC) lasers. WBC methods have been developed to combine beams along a combining dimension and produce a high power multi-wavelength output.

There are various known methods for making tunable diode or semiconductor lasers. These methods are: Littrow, Littman-Metcalf, and sampled grating. In both Littrow and Littman-Metcalf configurations wavelength tuning is accomplished by mechanically rotating the diffraction grating or mirror. However, there are disadvantages with these methods. For example, the tuning range for such a tunable laser is limited to the gain bandwidth of each diode emitter. Additionally, the wavelength tuning speed is very slow and is limited by the mechanical nature of the tuning mechanism. In a sampled grating approach, the tuning speed can be very fast. However, the tuning range is limited to the gain of the diode element.

The following application seeks to solve the problems stated.

SUMMARY OF THE INVENTION

Disclosed herein is a system and method for tuning an infrared source laser in the Mid-IR wavelength range. The system and method comprising, at least, a plurality of individually tunable emitters, each emitter emitting a beam having a unique wavelength, a grating, a mirror positioned after the grating to receive at least one refracted order of light of at least one beam and to redirect the beam back towards the grating, and a micro-electro-mechanical system (MEMS) device containing a plurality of adjustable micromirrors.

In at least one embodiment, a cavity consists of an individually addressable diode or QCL laser array, a transform lens, a diffraction grating, a second transform lens, and a digital micromirror device (DMD). In some embodiments, the cavity may be a conventional WBC.

In one exemplary embodiment, the QCL or diode array may consist of 20 emitters, each emitter having a previously specified gain peak. In such an embodiment the first emitter may have a gain peak at 6 µm and the adjacent emitter has a gain peak at 6.2 µm, wherein the gain peak of each element thereafter increments by 0.2 µm. Thus, enabling discrete wavelength tuning by switching on/off specified DMD mirrors. A DMD chip may have on its surface several hundred thousand microscopic mirrors arranged in an array which correspond to the pixels in an image to be displayed. The mirrors may be individually rotated ±10-12°, to an on or off state with the light being reflected to a beam dump. In the on state the light is stabilized and exits the system as a stabilized wavelength.

DETAILED DESCRIPTION OF THE PREFERRED EMBODIMENT

For purposes of this application optical elements may refer to any of lenses, mirrors, prisms and the like which redirect, reflect, bend, or in any other manner optically manipulate electromagnetic radiation. Additionally, the term beam includes visible light, infrared radiation, ultra-violet radiation, and electromagnetic radiation. Emitters include any beam-generating device such as semiconductor elements, which generate a beam, but may or may not be self-resonating. These also include fiber lasers, disk lasers, non-solid state lasers and so forth. Generally each emitter is comprised of at least one gain element. For example, a diode element is configured to produce a beam and has a gain element, which may be incorporated into a resonating system.

It should also be understand that certain emitters mentioned in embodiments below, such as a diode element, may be interchanged with other types of beam emitters.

DLP in industry is sometimes used to mean an array of individually controllable micromirrors, because these chips are sometimes called DLP chips and used in DLP projector systems. For this application, we prefer to use the term DMD digital micromirror device, which may be interpreted broadly to include any individually controllable array of reflectors, wherein the reflectors are small in size.

Figure 1:
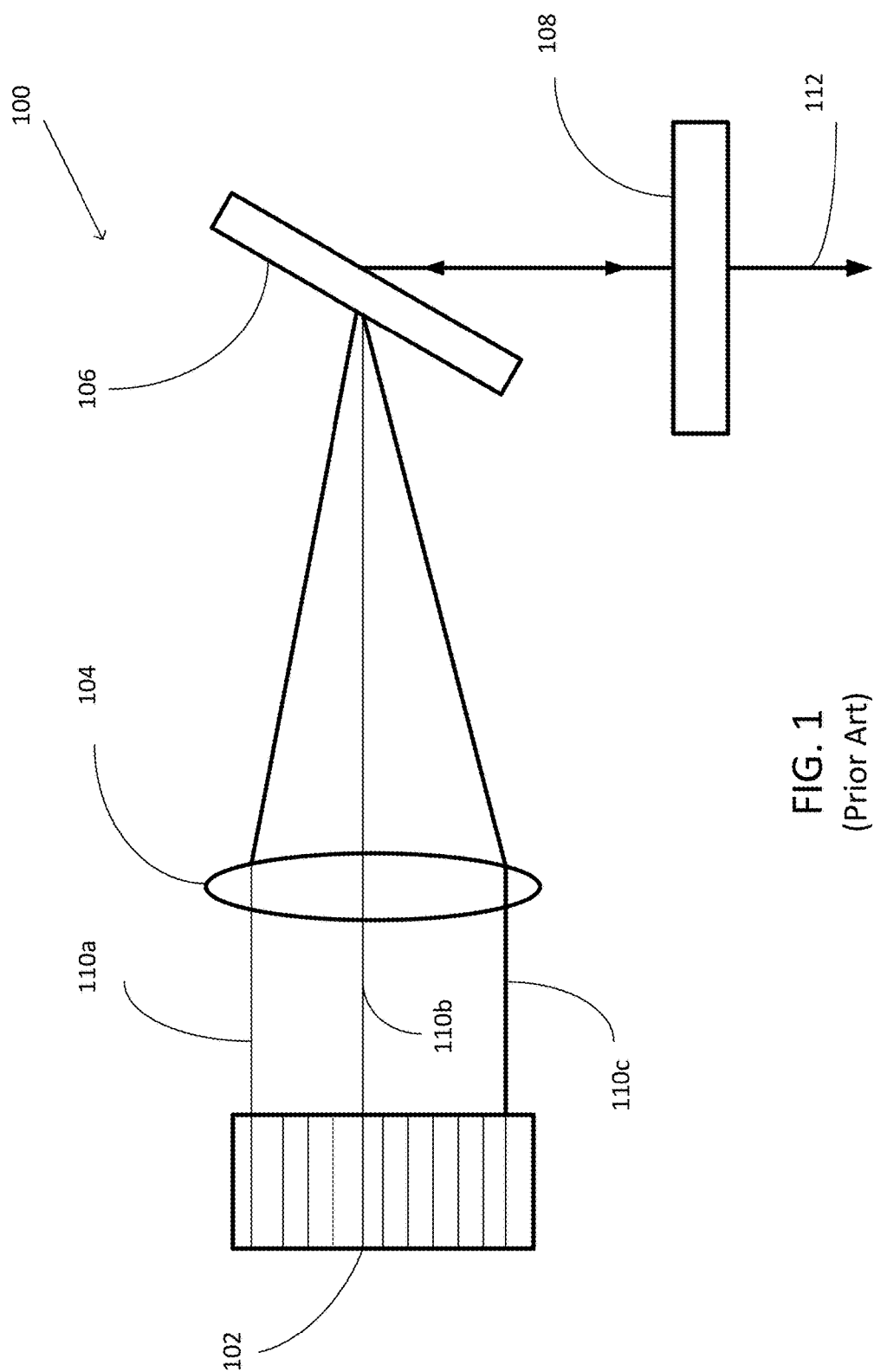
FIG. 1 illustrates a combining schematic of previous a WBC system.

FIG. 1 shows a WBC cavity 100. In WBC, an array of laser elements 102 is placed in an external cavity consisting of a transform lens 104, a diffraction grating 106, and an output coupler 108. Conceptually, WBC can be thought of as the spatial superposition of many independent diode laser external cavities. In the example shown in FIG. 1, three independent external cavities are shown 110a, 110b, and 110c. Each cavity has a distinct wavelength characteristic to that external-cavity-stabilized diode laser element. The diffraction grating 106 has an angle-to-wavelength conversion property that allows feedback to each diode laser element in the array, via the transform lens 104, at a different wavelength. Feedback from the output coupler stabilizes each of the individual emitters. WBC allows for brightness scaling of a diode laser array because all of the laser elements are spatially overlapped at the output coupler, maintaining the output beam quality of a single element while scaling the output power by the number of elements in the array. Wavelength beam combining can be applied to any laser with a gain bandwidth. For example, these lasers may include diode lasers, fiber lasers, CO2 lasers, and/or Quantum Cascade Lasers (QCLs).

Wavelength beam combining (WBC) is an incoherent process and, thus, does not require phasing of laser elements. In some embodiments, the brightness of the output beam 112 scales proportionally to the total number of laser elements. The output beam 112 of a WBC system is that of a single beam. In both coherent and WBC systems, the output beam quality is the same as that of a single emitter but the output power scales the power from all the laser elements. If both very high spectral brightness (single frequency operation) and very high spatial brightness (single spatial mode) is required then coherent beam combination is the only method. However, in many cases single frequency operation is not desired and may be detrimental to the functionality of the system, thus making WBC the preferred approach.

Figure 2:
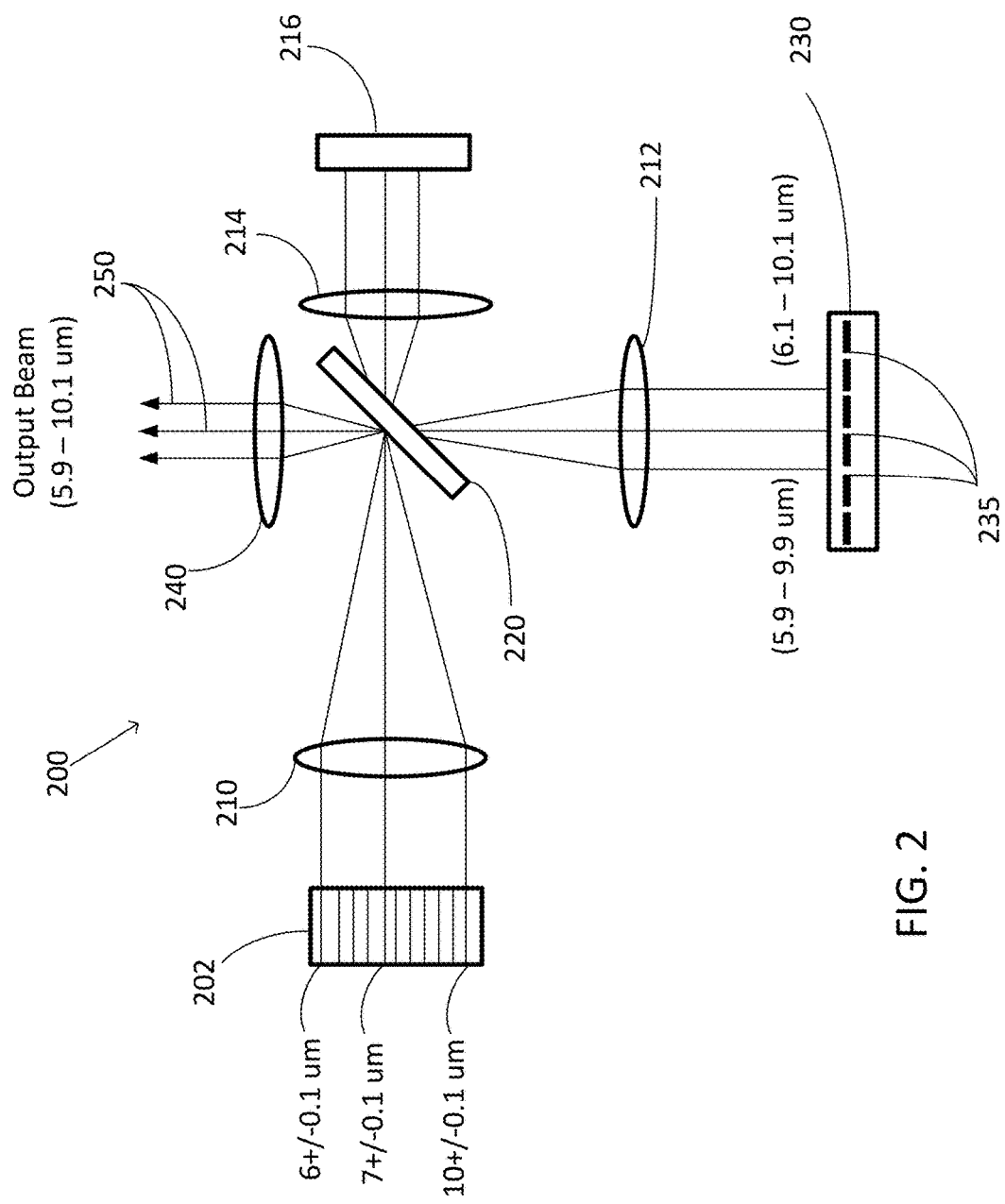
FIG. 2 illustrates a widely tunable infrared source laser system.

FIG. 2 illustrates at least one embodiment of the current disclosure. The widely tunable IR cavity 200 consists of an individually addressable diode or QCL laser array 202, a first optical element 210, a diffraction grating 220, a second optical element 212, an array of individually addressable micromirrors 235 such as a DMD 230, a third optical element 214, a reflective mirror 216, and a fourth optical element 240. The optical elements 210, 212, 214, and 240 may be transform lenses or collimating lenses having focal power along one or more planes. For example, 210 may cause individual beams emitted from 202 to converge onto grating 220. Optical element 240 may be used as a collimation lens for the stabilized output beams 250.

As shown, beams are emitted from 202 and converge onto 220. It should be understood that 210, which causes the beams to be angled individually onto grating 220 may be absent. In other embodiments, where each individual emitter is mechanically positioned to converge on to grating 220, this still allows for the angle-to-wavelength conversion property of grating 220 to provide feedback into each mechanically positioned emitter at a different wavelength.

After the beams are caused to converge onto grating 220 orders of diffracted light occur. In one instance the 0th order beam is used to re-image onto a mirror 216. The reflected beam is overlapped onto the diffraction grating. The output beam is then taken off the 1st order in combination with a chief-ray collimation lens (this would be 240 in FIG. 2). The chief-ray collimation lens enables the output to be co-boresighted. A co-boresighted system is important for many applications such as various spectroscopy systems including: conventional absorption spectroscopy of trace chemical and biological agents, improvised explosive detection, differential absorption lidar (DIAL), and multi-wavelength photo-acoustic spectroscopy, material verification, anti-counterfeiting, and threat screening.

As mentioned the orders that are diffracted from 220 in the tunable cavity system 200 may be recycled and used as feedback mechanisms to stabilize the individual emitters of 202. Lenses 212 and 214 assist in collimating the diffracted beams and upon being reflected cause the reflected beams to converge back onto the grating. Reflective mirror 216 is such a mirror that helps overlap and recycle these orders.

In some embodiments, the cavity 200 may be a conventional WBC. In such embodiments, discrete wavelength tuning of each element may be possible. At any given time there may be only one beam exiting hitting the DMD 230, which is accomplished by switching off all but one of the DMD mirrors 235.

In some embodiments, the cavity 200, may act as a conventional WBC cavity with the exception of not extracting the output beam from DMD 235. To illustrate this point assume in one exemplary embodiment, the QCL or diode array 202 consists of 20 emitters, each emitter having a previously specified gain peak ranging from 6 µm-10.0 µm. Each subsequent element in between has a gain peak incrementing by 0.2 µm. For example, in such embodiments, the middle element has a gain peak at 7 µm and the last element has a gain peak at 10 µm. If the middle mirror of the DMD 230 is turned on and all other DMD mirrors 235 are turned off, then all 20 elements will lase at the unique wavelength at an increment of 0.2 µm. For example, in such embodiments the wavelengths are 6 µm, 6.2 µm, 6.4 µm . . . 9.6 µm, 9.8 µm, and 10.0 µm.

Consistent with the present disclosure, are systems wherein if the left most DMD mirror is turned on and all other DMD mirrors are turned off then the first emitter will lase at a wavelength of 5.9 µm, the adjacent elements will lase at wavelengths in increments of 0.2 µm, and the last element will lase at 9.9 µm. In FIG. 2, this is shown schematically as the left most beam between the grating 220 and the DMD chip 230. If the right most DMD mirror is turned on and all of other DMD mirrors are turned off then the first emitter will lase at 6.1 µm and the adjacent element will lase at wavelengths in increments of 0.2 µm, and the last element will lase at 10.1 µm. In FIG. 2, this is shown schematically as the right most beam between the grating 220 and DMD 230. Thus, in principle any wavelength can be accessed by simply switching the proper DMD mirror and turning on the proper diode element. The total number of DMD mirrors is dictated by the total number of wavelengths per unit diode (QCL) element. For example, in embodiments where 100 wavelengths per element are desired at least 100 DMD mirrors are required. In such embodiments conventional DMD chips may be used. Higher numbers of wavelengths are also contemplated herein. Turning on any wavelength can be accomplished very quickly since the settling time of the DMD mirror can be as fast as 10 µs.

Contemplated herein are methods to extract higher amounts of useable output power. In at least one embodiment, extracting higher amounts of useable output power can be achieved by inserting a beam splitter inside the cavity.

In the embodiment illustrated in FIG. 2 the 0th order output beam 250 is used to re-image onto a mirror 216. In this embodiment, the reflected beam is overlapped onto the diffraction grating 220. The output beam is taken off the 1st order in combination with a chief-ray collimation lens 240. In some embodiments, regardless of the wavelength, a chief-ray collimation lens 240 may ensure that the output beam 250 is co-bore sighted.

Further in FIG. 2, the embodiment depicted includes a QCL array of 20 emitters and is 10 mm wide. In embodiments having a grating dispersion of 150 lines per mm, then the required transform lens 210 has a focal length of about 10 mm. This optical setup of this embodiment will dictate a total optical bandwidth of about 4000 nm. The second transform lens 212 and grating 220 help dictate the tuning of each emitter. For example, in embodiments where each emitter is tunable to about 200 nm and the pitch of the DMD is 10 μm, the focal length of the second transform 212 lens is 5 mm. Thus, the total optical path length from the diode array to the DMD chip, in this embodiment is very compact in size. In at least one embodiment the total optical path length from the diode array to the DMD chip is about 30 mm.

Consistent with the present disclosure are systems having a grating element. In at least one embodiment, a transmission grating may be preferable, while in other embodiments, a reflection grating may be desired.

Figure 3:
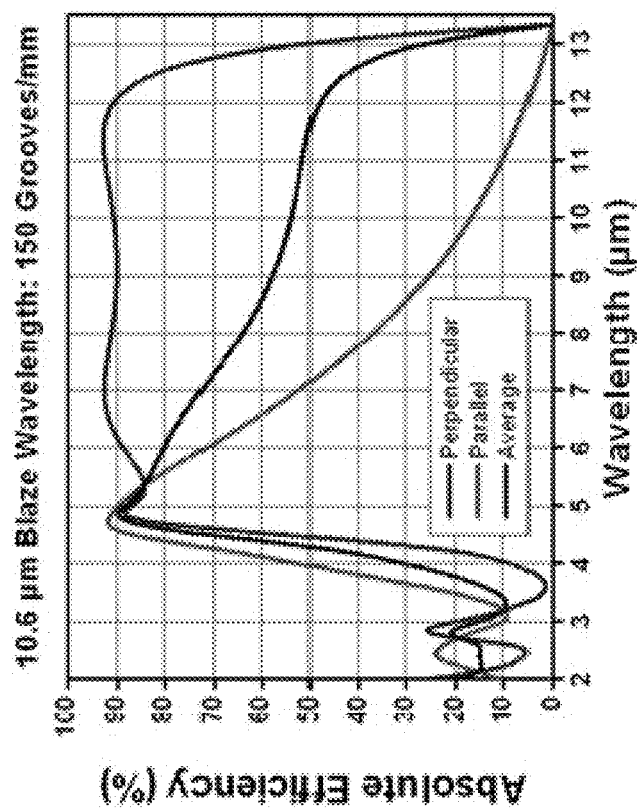
FIG. 3 illustrates the efficiency of at least one embodiment of grating, 150 l/mm, used on a widely tunable infrared source laser system.

FIG. 3 depicts an efficiency curve of a system, in accordance with the present disclosure, having a reflection grating. The efficiency of the grating is >90% from 5-12 μm.

Consistent with the present disclosure are systems having individually addressable array of quantum cascade laser (QCL) elements. In such embodiments, electric tuning may be accomplished by turning on only one element of the array at a time. Each laser element may be wavelength locked to a unique wavelength that is linearly chirped in the array. Thus, in such embodiments, wavelength tuning over the entire 6-10 μm range may be accomplished and the single output beam would the same characteristics and beam quality as a single element that is turned on. Due to the nature of wavelength tuning disclosed. In such embodiments, within a given element, the wavelength shift may be about 200 nm and the total bandwidth of the system may 4000 nm. As a result, it is contemplated that a smearing of the near field may occur at about 200 nm/4000 nm=5%.

Quantum Cascade Laser (QCL) Sources

Figure 4:
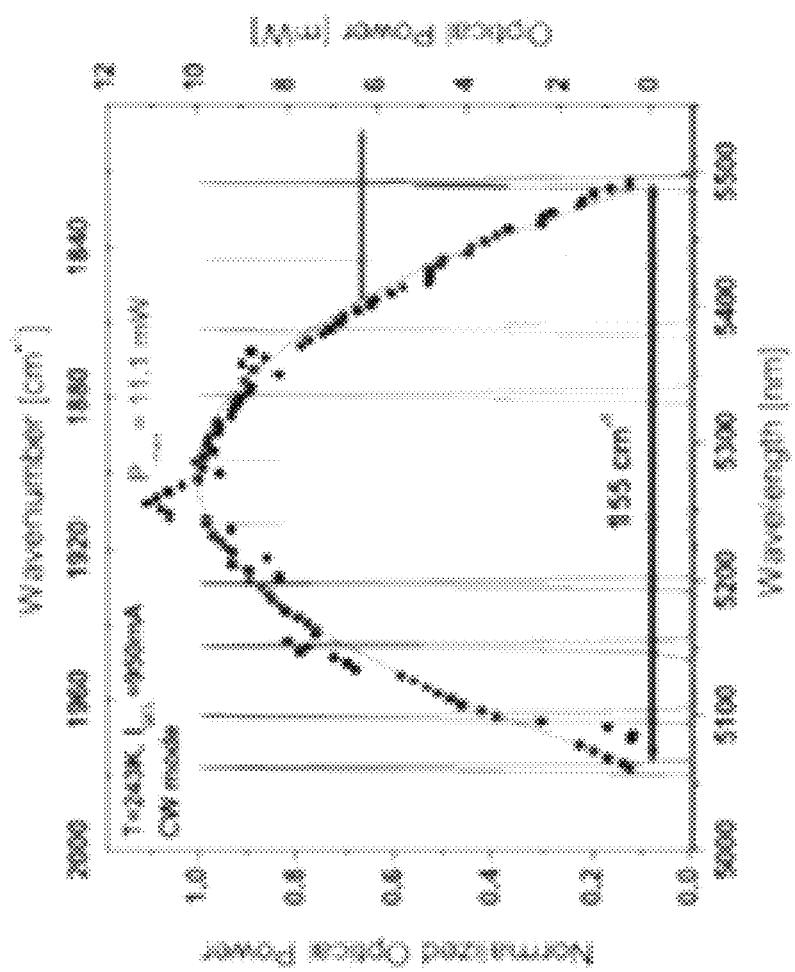
FIG. 4 illustrates the tuning range of a 5 micron wavelength quantum cascade laser.

In order to meet the broad wavelength coverage requirement for 6 to 10 μm, as described for at least one embodiment above, QCLs having a tuning range of 100 to 200 nm per QCL may be desired. A spectral bandwidth of 200 nm may be supported by the tuning range or gain bandwidth of the laser element. FIG. 4 shows a typical tuning range of a 5 μm-wavelength quantum cascade laser which tunes between 5050 nm and 5500 nm, thus having about a 500-nm tuning range. However, in additional embodiments a more usable tuning range is about 250 nm or 80% of maximum power. The tuning range scales with the wavelength and may become larger in the range of 6-10 μm. In additional embodiments, a single QCL wafer can be grown epitaxially to cover the wavelength range of 6-10 μm by employing multiple gain regions with different center wavelengths within the same laser structure.

In at least one embodiment, as many as 40-50 QCLs may be used to cover the desired wavelength range. Redundancy of QCLs may be used in some embodiments to help ensure reliable operation. With 40 QCLs for example, the tuning step size may be 100 nm.

Figure 5B:
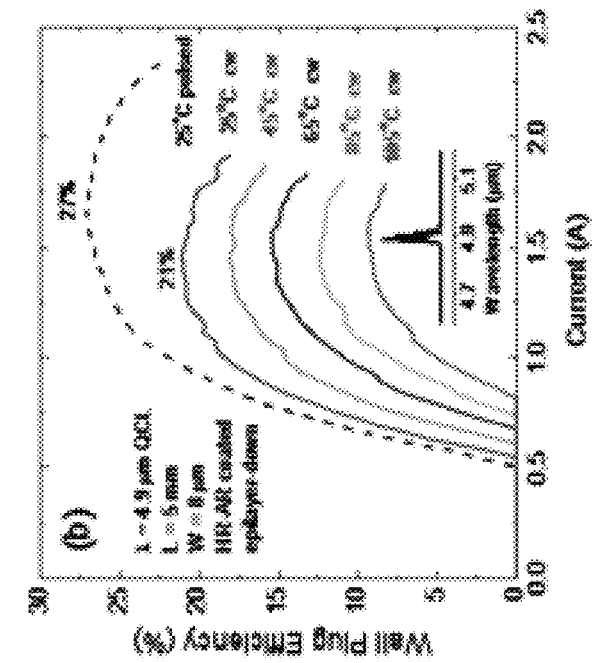
FIG. 5B illustrates the wall-plug efficiency of an MWIR QCL at 4.9 center wavelength under CW and pulsed operation of a widely tunable infrared source laser system.
Figure 5A:
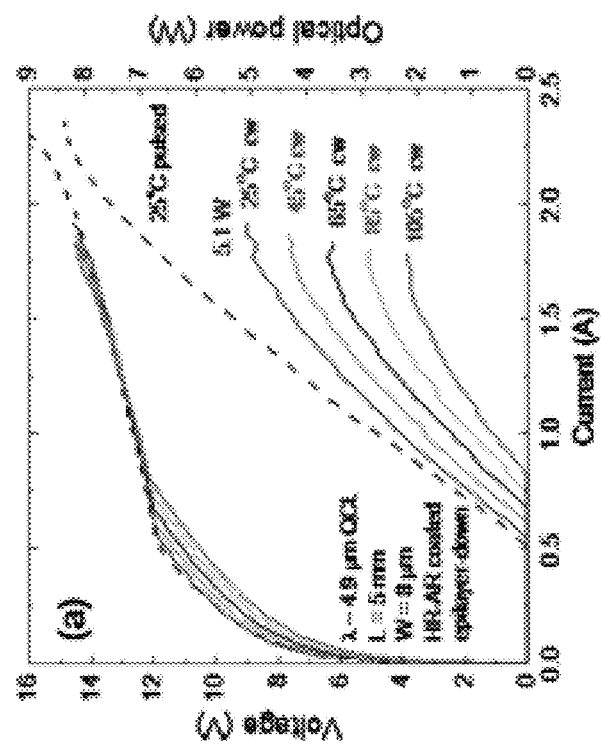
FIG. 5A illustrates the L-I-V characteristics of a mid-wavelength infrared (MWIR) quantum cascade laser (QCL) at 4.9 center wavelength under continuous wave (CW) and pulsed operation of a widely tunable infrared source laser system.

In some embodiments, lasing sources may be single emitter, single transverse mode semiconductor QCLs. In order to obtain a desired power and a diffraction limited output power, single emitter diodes may be used and mounted on a common heat-sink. In at least one embodiment, the diode may be mounted on a heat-sink using discrete device packaging technology; however other mounting technologies commonly known in the art are also consistent with the present disclosure. In at least one embodiment, each device is lensed with collimating optics. FIGS. 5A-B demonstrate a single element power and efficiency Quantum Cascade Lasers (QCLs) having 5.1 W CW (8.3 W pulsed) room temperature QCLs at 4.9 μm wavelength in a single spatial mode. The maximum wall plug efficiency (WPE) under CW operation is 21% and under pulsed operation the maximum WPE is 27%. FIG. 5A shows L-I-V characteristics under CW and pulsed operation while FIG. 5B shows wall-plug efficiency under CW and pulsed operation.

Figure 6B:
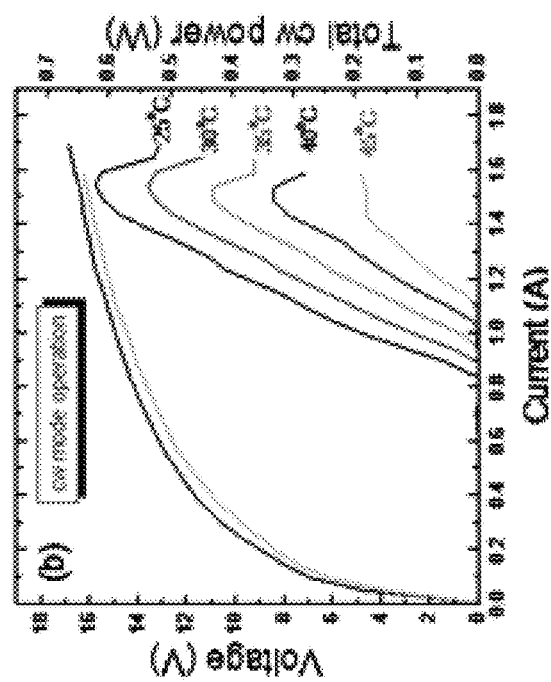
FIGS. 6A and 6B illustrate the L-I-V characteristics of a long-wavelength infrared (LWIR) quantum cascade laser (QCL) at approximately 10.2 microns center wavelength under pulsed operation (FIG. 6A) and continuous wave operation (FIG. 6B) of a widely tunable infrared source laser system.
Figure 6A:
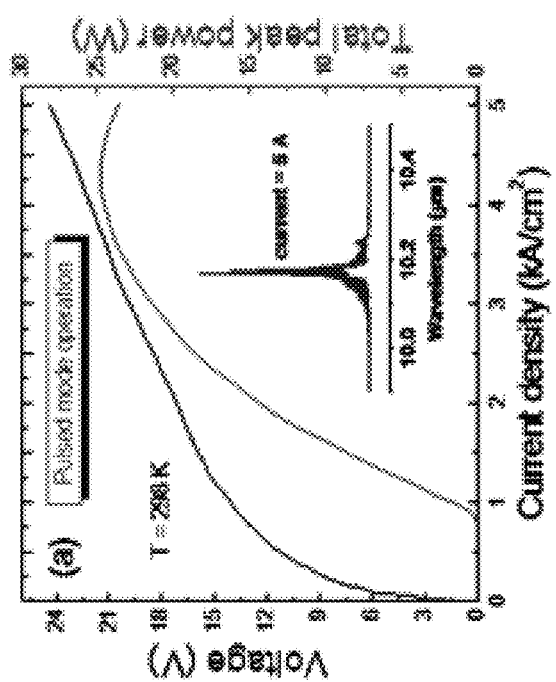

As shown in FIGS. 6A-B, in some embodiments, high power, efficient QCLs at longer wavelengths in the LWIR, including 10 microns, may also be used. The high power QCL of this embodiment, obtains up to 25 W in peak power and >0.5 W under room temperature, CW operation. The device may still operate under CW operation at a temperature of 45 C.

Digital Light Processing (DLP aka DMD) Chip

In some embodiments, the fine tuning within each 100 nm band may be accomplished using a tunable component in the WBC external cavity. The specification that drives this requirement is the tuning step time of 125 sec (threshold) and 31 μsec (objective). One can select a DLP chip that allows for this very fast tuning. See FIG. 2 for the implementation of the entire design, with the individually addressable QCL array for the coarse wavelength tuning (100 nm resolution) and the fast DLP array for fine wavelength tuning (0.5 nm resolution).

In at least one embodiment, the DLP chip is a MEMS-based device and has no large mechanical moving parts.

Control Electronics and Software

In some embodiments, control electronics and software may be used to apply current to the individually addressable QCL array and operate the DMD chip as required for the electronic wavelength tuning. In such embodiments, the QCLs may operate under pulsed operation, operated by a pulsed QCL driver. In some embodiments, the control software may have wavelength sweep modes, ramp modes, and/or any other modes commonly used in the art.

In at least one embodiment, coarse wavelength tuning may be accomplished by switching the specific QCL of interest in the array. In additional embodiments, fine wavelength tuning may be accomplished by adjusting the DMD mirror corresponding to that particular device. By adjusting the DMD mirror, electrical power may be applied to all elements of the QCL array constantly, and wavelength tuning may be accomplished by adjusting the DMD mirror for feedback to a single element within the QCL array.

Although the focus of this application has been on the MID-IR range, the principles may apply to wavelengths outside of those ranges that are determined by the emitters and gratings used.

The above description is merely illustrative. Having thus described several aspects of at least one embodiment of this invention including the preferred embodiments, it is to be appreciated that various alterations, modifications, and improvements may readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method of tuning a beam source, the method comprising:

providing a plurality of beam emitters each emitting a beam having a different wavelength;

converging the beams emitted by the beam emitters onto a grating, whereby the beams are split into a plurality of orders;

reflecting a first one of the orders through the grating and back to the plurality of beam emitters, whereby each beam is reflected back to the beam emitter from which it was emitted to thereby stabilize the beam to its different wavelength;

receiving a second one of the orders at an array of individually controllable reflectors; and redirecting one or more of the beams within the second one of the orders, with one or more of the reflectors, back to the grating, whereby the one or more of the beams are transmitted as one or more tuned output beams.

2. The method of claim 1, wherein the beams emitted by the beam emitters are converged onto the grating at least in part by an optical element.

3. The method of claim 1, wherein convergence of the beams onto the grating arises at least in part due to positioning of beam emitters to emit beams that converge toward each other.

4. The method of claim 1, wherein the grating comprises a reflective diffraction grating or a transmissive diffraction grating.

5. The method of claim 1, further comprising redirecting one or more of the beams within the second one of the orders, with one or more of the reflectors, to a beam dump.

6. The method of claim 1, further comprising collimating one or more of the tuned output beams.

7. The method of claim 1, wherein the first one of the orders is reflected back to the plurality of beam emitters by a mirror, the mirror being spaced apart from the grating.

8. The method of claim 1, wherein the array of individually controllable reflectors is at least a portion of a micro-electro-mechanical systems device.

9. The method of claim 1, wherein the array of individually controllable reflectors is at least a portion of a digital light processing chip.

10. The method of claim 1, wherein at least one of the beam emitters comprises a quantum cascade laser source.

11. A method of tuning a beam source, the method comprising:

providing a plurality of beam emitters each emitting a beam having a different wavelength;

converging the beams emitted by the beam emitters onto a grating;

after converging the beams onto the grating, reflecting a first portion of each beam back to the beam emitter by which it was emitted to thereby stabilize the beam to its different wavelength;

after converging the beams onto the grating, for at least one of the beams, reflecting a second portion of the beam, with one of a plurality of individually controllable reflectors, as a tuned output beam in a direction away from the plurality of beam emitters.

12. The method of claim 11, wherein the beams emitted by the beam emitters are converged onto the grating at least in part by an optical element.

13. The method of claim 11, wherein convergence of the beams onto the grating arises at least in part due to positioning of beam emitters to emit beams that converge toward each other.

14. The method of claim 11, wherein the grating comprises a reflective diffraction grating or a transmissive diffraction grating.

15. The method of claim 11, further comprising, for at least one of the beams, reflecting a second portion of the beam, with one of the plurality of individually controllable reflectors, to a beam dump.

16. The method of claim 11, further comprising collimating the tuned output beam.

17. The method of claim 11, wherein the first portion of each beam is reflected back to the plurality of beam emitters by a mirror, the mirror being spaced apart from the grating.

18. The method of claim 11, wherein the array of individually controllable reflectors is at least a portion of a micro-electro-mechanical systems device.

19. The method of claim 11, wherein the array of individually controllable reflectors is at least a portion of a digital light processing chip.

20. The method of claim 11, wherein at least one of the beam emitters comprises a quantum cascade laser source.

* * * * *